United States Patent
Riebman et al.

(10) Patent No.: US 7,066,874 B2
(45) Date of Patent: Jun. 27, 2006

(54) DEVICES AND METHODS FOR BLOOD FLOW ASSISTANCE

(75) Inventors: Jerome B. Riebman, Sunnyvale, CA (US); Kevin L. Ohashi, Jamaica Plain, MA (US)

(73) Assignee: Bay Innovation Group, LLC, Sunnyvale, CA (US)

( * ) Notice: Subject to any disclaimer, the term of this patent is extended or adjusted under 35 U.S.C. 154(b) by 163 days.

(21) Appl. No.: 10/751,405

(22) Filed: Jan. 6, 2004

(65) Prior Publication Data
US 2005/0148810 A1    Jul. 7, 2005

(51) Int. Cl.
*A61N 1/362* (2006.01)
(52) U.S. Cl. .................................... 600/16
(58) Field of Classification Search ............... 600/16, 600/17; 623/3.1, 3.2, 3.21
See application file for complete search history.

(56) References Cited

U.S. PATENT DOCUMENTS

| | | | |
|---|---|---|---|
| 3,568,214 A * | 3/1971 | Goldschmied | 623/3.21 |
| 3,585,983 A | 6/1971 | Kantrowitz et al. | |
| 3,707,960 A | 1/1973 | Freed | |
| 3,866,604 A | 2/1975 | Curless et al. | |
| 3,911,898 A | 10/1975 | Leachman, Jr. | |
| 3,955,557 A | 5/1976 | Takagi | |
| 3,974,825 A * | 8/1976 | Normann | 600/17 |
| 3,978,187 A | 8/1976 | Fletcher et al. | |
| 4,004,299 A | 1/1977 | Runge | |
| 4,034,742 A | 7/1977 | Thoma | |
| 4,051,840 A | 10/1977 | Kantrowitz et al. | |
| 4,058,855 A | 11/1977 | Runge | |
| 4,080,958 A | 3/1978 | Bregman et al. | |
| 4,092,742 A | 6/1978 | Kantrowitz et al. | |
| 4,116,589 A | 9/1978 | Rishton | |
| 4,144,595 A | 3/1979 | Unger | |
| 4,192,293 A | 3/1980 | Asrican | |
| 4,195,623 A | 4/1980 | Zeff et al. | |
| 4,204,524 A | 5/1980 | Martin et al. | |
| 4,222,127 A | 9/1980 | Donachy et al. | |
| 4,231,354 A | 11/1980 | Kurtz et al. | |
| 4,240,409 A | 12/1980 | Robinson et al. | |
| 4,245,622 A | 1/1981 | Hutchins, IV | |
| 4,369,530 A | 1/1983 | Robinson et al. | |
| 4,376,312 A | 3/1983 | Robinson et al. | |
| 4,427,470 A | 1/1984 | Kolff | |
| 4,473,423 A | 9/1984 | Kolff | |
| 4,510,628 A | 4/1985 | Kolff | |
| 4,527,549 A | 7/1985 | Gabbay | |

(Continued)

FOREIGN PATENT DOCUMENTS
EP    0074733 B1    3/1983

OTHER PUBLICATIONS
MedTerms Medical Dictionary, www.medterms.com, defined: mediastinum.*

(Continued)

*Primary Examiner*—Jeffrey R. Jastrzab
*Assistant Examiner*—Alyssa M. Alter
(74) *Attorney, Agent, or Firm*—Moazzam & Associates, LLC

(57) ABSTRACT

Devices and methods are disclosed for assisting in blood flow from a weakened or injured heart, particularly for pediatric patients. A low profile, multi-chambered implantable mechanism is used to collect blood from a blood vessel and re-pump the blood out with an induced pressure emanating from a fluid pressure source. The devices and methods described herein are easy to use and may be attachable to body tissue without use of suture anastomosis.

47 Claims, 5 Drawing Sheets

U.S. PATENT DOCUMENTS

| | | | |
|---|---|---|---|
| 4,573,997 | A | 3/1986 | Wisman et al. |
| 4,630,597 | A | 12/1986 | Kantrowitz et al. |
| 4,692,148 | A | 9/1987 | Kantrowitz et al. |
| 4,733,652 | A | 3/1988 | Kantrowitz et al. |
| 4,741,328 | A | 5/1988 | Gabbay |
| 4,753,226 | A | 6/1988 | Zheng et al. |
| 4,771,765 | A | 9/1988 | Choy et al. |
| 4,781,715 | A * | 11/1988 | Wurzel ................ 623/3.21 |
| 4,822,357 | A | 4/1989 | Forster et al. |
| 4,838,889 | A | 6/1989 | Kolff |
| 4,863,461 | A | 9/1989 | Jarvik |
| 4,902,291 | A | 2/1990 | Kolff |
| 4,976,729 | A | 12/1990 | Holfert et al. |
| 5,089,020 | A | 2/1992 | Koppert |
| 5,171,207 | A | 12/1992 | Whalen |
| 5,254,097 | A | 10/1993 | Schock et al. |
| 5,256,132 | A | 10/1993 | Snyders |
| 5,273,518 | A | 12/1993 | Lee et al. |
| 5,282,849 | A | 2/1994 | Kolff et al. |
| 5,324,464 | A | 6/1994 | Holfert et al. |
| 5,332,403 | A | 7/1994 | Kolff |
| 5,397,349 | A | 3/1995 | Kolff et al. |
| 5,413,549 | A | 5/1995 | Leschinsky |
| 5,429,584 | A | 7/1995 | Chiu |
| 5,453,076 | A | 9/1995 | Kiyota et al. |
| 5,487,722 | A | 1/1996 | Weaver, II et al. |
| 5,554,103 | A | 9/1996 | Zheng et al. |
| 5,658,237 | A | 8/1997 | Francischelli |
| 5,738,627 | A | 4/1998 | Kovacs et al. |
| 5,749,839 | A | 5/1998 | Kovacs |
| 5,776,047 | A | 7/1998 | Fukunaga et al. |
| 5,817,001 | A | 10/1998 | Leschinsky et al. |
| 5,908,378 | A | 6/1999 | Kovacs et al. |
| 5,910,103 | A | 6/1999 | Saper et al. |
| 5,928,132 | A | 7/1999 | Leschinsky |
| 5,997,540 | A | 12/1999 | Zheng et al. |
| 6,007,479 | A | 12/1999 | Rottenberg et al. |
| 6,066,085 | A | 5/2000 | Heilman et al. |
| 6,123,725 | A | 9/2000 | Aboul-Hosn |
| 6,146,372 | A | 11/2000 | Leschinsky et al. |
| 6,191,111 | B1 | 2/2001 | Leschinsky |
| 6,200,260 | B1 | 3/2001 | Bolling |
| 6,251,061 | B1 | 6/2001 | Hastings et al. |
| 6,254,525 | B1 | 7/2001 | Reinhardt et al. |
| 6,398,714 | B1 | 6/2002 | Verkerke et al. |
| 6,406,422 | B1 | 6/2002 | Landesberg |
| 6,450,942 | B1 | 9/2002 | Lapanashvili et al. |
| 6,579,223 | B1 * | 6/2003 | Palmer ................ 600/16 |
| 6,669,726 | B1 * | 12/2003 | Giambruno ............ 623/3.17 |
| 2002/0095210 | A1 | 7/2002 | Finnegan et al. |

OTHER PUBLICATIONS

Riebman, Jerome B., "Extra-Aortic Counterpulsation Assistance for the Failing Pediatric Heart: A Novel New Approach," presented at New Era Cardiac Conf., Jan. 7, 2003.

Riebman, Jerome B., "Extra-Aortic Counterpulsation Assistance for the Failing Pediatric Heart: A Novel Approach," slide presentation at New Era Cardiac Conf., Jan. 7, 2003.

Sakurai, H., et al., "Aortic Dissection in an Infant Caused by Intraortic Balloon Pumping," Pedatr. Cardiol. 1999, Sep.-Oct.; 20(5): 373-4.

Zelano, John A., et al., "Comparison of an Extraaortic Counterpulsation Device Versus Intraortic Balloon Pumping in Severe Cardiac Failure", ASAIO Trans 1991; 37; M342-M344.

Feola, Mario, et al., "Intraortic Balloon Pumping in the Experiemntal Animal," Am Journal of Cardiology, vol. 27, Feb. 1971, pp. 129-136.

Pennington, D. Glenn, et al., "Circulatory Support in Infants and Children," Ann Thorac Surg, 1993; 55; pp. 233-237.

Pantalos, G., et al., "In Vivo Evaluation of IABP Function in an Infant Animal Model of LV Dysfunction," ASAIO 43:2, Apr./Mar. 1997, abstr.

Nanas, John N., et al., "Hemodynamic Effects and Biocompatibility of a Valveless Implantable Abdominal Aortic Counterpulsation Device (AACD)", Circut, 70 Supp II, Oct. 1984, abst.

Nanas, SN, et al., "Effectiveness of the Para-Aortic Counterpuls. Device Implanted on the Ascending Aorta vs. Centr. Blood Pump in Cardiog. Shock," XIX ESAO Congr, Oct. 1992, abst.

Gitter, Richard, et al., "Influence of Ascending Versus Descending Balloon Counterpulsation on Bypass Graft Blood Flow," Ann Thorac Surg 1998; 65; pp. 365-370.

Reinhartz, Olaf, et al., "Current Clinical Status of Pulsatile Pediatric Circulatory Support," ASAIO Journal 2002; 48, pp. 455-459.

Trumble, Dennis R., et al., "Copulsation Bailloon for Right Ventricular Assistance," Circulation, 1999, 99, pp. 2815-2818.

Kolff, Willem J., "The Need for Easier Manufact. of Artificial Hearts and Assist Devices and How This Need Can be Met by the Vacuum Mold. Techniq.," ASAIO Jour 1998, pp. 12-27.

Akomea-Agyin, Clement, et al., "Intraaortic Balloon Pumping in Children," Ann Thorac Surg 1999; 67, pp. 1415-1420.

Fischer, Edmundo, et al., "A New Approach to Assist Postoperative Heart Failure in an Animal Model: Juxta-Aortic Counterpulsation," Artificial Organs, 26(10), pp. 819-826.

Konert, Wolfgang, et al., "Clinical Experience with the MEDOS HIA-VAD Susyem in Infants and Children: A Preliminary Report," Ann. Thorac Surg 1997, 63, pp. 1138-1144.

Merkle, Frank, et al., "Pulsatile Mechanical Cardiac Assistance in Pediatric Patients with the Berlin Heart Ventricular Assist Device," JECT 2003, 35, pp. 115-120.

Bian, Xiaoming, et al., "Enh. Intra-Aortic Ball Pump: Marked. Impr. Syst Hemod and Card. Func. in Canines with Sev., Acute Lf Ventr Failure," Artif Organs 2002, 26(8), 727-733.

Minich, L. LuAnn, et al., "In Vitro Evaluation of the Effect of Aortic Compliance on Pediatric Intra-Aortic Ballloon Pumping," Pediatr Crit Care Med 2001, 2(2), pp. 139-144.

Utoh, J., et al., "Chronic In Vivo Function of a New Ventricular Assist Device: The Extracorporeal Pulsatile Assist Device (EPAD)," Intl J of Artif Organs, 16(2), pp. 91-95.

Ide, Hirofumi, et al., "Eval of the Pulsatility of a New Puls Lf Ventric Asst Dev—The Integrated Cardioassist Cath—in Dogs," J Thorac Cardiovasc Surg 1994, 107, 569-575.

Park, Jeanny, et al., "Intraortic Balloon Pump Management of Refractory Congestive Heart Failure in Children," Pediatr Cardiol 1993, 14, pp. 19-22.

Nido, P.J., et al., "Successful Use of Intraortic Balloon Pumping in a 2-Kilogram Infant," Ann Thorac Surg, Nov. 1988, 46(5), pp. 574-576.

Moulopoulis, S.D., "3. Systolic Counterpulsation with a Small Balloon to Increase Coronary Flow," Assisted Circulation 2, Springer-Verlag, 1984, pp. 38-41.

Nanas, J.N., et al., "Hemodynam Effects of an Implanted Abdom Aortic Counterpuls Device Designed for Chrnic Use in Graded Heart Failure," Life Supp Syst 1985, 3(Supp 1), 245-9.

Scheidt, Stephen, et al., "Mechanical Circ Asst with the Intraaortic Balloon Pump and Other Counterpulsation Devices," Progr Cardiovasc Dis, XXV (1), Jul./Aug. 1982, pp. 55-76.

Taenaka, Y., et al., "Ventricular Assist Device (VAD) for Children; In Vitro and In Vivo Evaluation," Trans Am Soc Artif Intern Organs 1984, XXX, pp. 155-158.

Taenaka, Y., et al., "A Pediatr Ventr Asst Dev: Its Develop and Experim Eval of Hemodyn Effects on Postop Heart Fail of Congen Heart Diseases," Artif Organs 1990, 14(1), 49-56.

Nojiri, Chisato, et al., "Small Sft Left Ventr Asst Dev Powered by Intraaortic Balloon Pump Console for infants: A Less Expensive Option," Artif Organs 1992, 16(4), 382-385.

Charitos, C.E., et al., "Right and Left Ventric Interaction in Ventricular Fibrill Under Mechanical Assistance," ESAO Congr, Oct. 1992, abstr.

Nanas, J.N., et al., "A Relief Valve Placed on an IABP Driving System Made it Proper for Driving a Left Ventricular Assist Device," ESAO Congr, Oct. 1992, abstr.

Nanas, J., et al., "Hemodynamic Effects of a Counterpulsation Device Implanted on the Ascending Aorta in an Acute Heart-Failure Model," ASAIO abstrs 1987.

Weinhaus, Larry, et al., "Extracorpporeal Membrane Oxygenation for Circulatory Support After Repair of Congenital Heart Defects," Ann Thorac Surg 1989, 48, pp. 206-212.

Moat, N.E., et al., "Circulat Support in Infants with Post-Cardiopulm Bypas Left Ventric Dysfunct Using a Left Ventric Assist Device," Eur J Cardio-thorac Surg 1990, 4, 649-52.

Sanfelippo, Peter, et al., "Experience with Intraaortic Balloon Counterpulsation," Ann Thorac Surg, 1986, 41, pp. 36-41.

Veasy, George, et al., "Intra-aortic Balloon Pumping in Infants and Children," Circulation 1983, 68 (5), pp. 1095-1100.

Christensen, David, et al., "Intra-Aortic Balloon Counterpulsation in Children: A Review of 29 Patients," Critical Care Medicine 1991, 19(575), Suppl, abst.

Veasy, George, et al., "Intra-Aortic Balloon Pumping: Adaptation for Pediatric Use," Critical Care Clinics, 2(2), Apr. 1986, pp. 237-249.

Grayzel, Joseph, "Clinical Evaluation of the Percor Percutaneous Intraortic Balloon: Cooperative Study of 722 Cases," Circulation 66 (suppl I), 1982, pp. I-223-I-226.

Bregman, David, et al., "Percutaneous Intraaortic Balloon Pumping: Initial Clinical Experience," Ann Thorac Surg, 29(2), Feb. 1980, pp. 153-155.

Nanas, John, et al., "Preclinical Evaluation of the Abdominal Aortic Counterpulsation Device," Am Heart J 1988, 116, pp. 1003-1008.

Nanas, John, et al., "Effectiveness of a Counterpulsation Device Implanted on the Ascending Aorta," Trans Am Soc Artif Organs 1987, XXXIII, pp. 203-206.

Nanas, John, "Superiority of Implanted Abdom Aortic Counterpuls Device Des for Chronic Use Comp to Intraaortic Balloon Pump," Circulation, 72 (supp III). Oct. 1985, abstr.

Nanas, John, et al., "Hemodyn Effects of a Counterpuls Dev Implanted on the Ascending Aorta in Severe Cardiogenic Shock," ASAIO Trans 1988, 34, pp. 229-234.

Zelano, John, et al., "Evaluation of an Extraaortic Counterpulsation Device in Severe Cardiac Failure," Ann Thorac Surg 1992, 53, pp. 30-37.

Stiller, Brigitte, et al., "Heart Transplant in Children After Mech Circul Support with Pulsatile Pneumatic Assist Device," J Heart Lung Transplant, 2003, 22, pp. 1201-1208.

Intra-Vasc brochure, Pulsatile Catheter Pumps, Aug. 5, 2003, 2 pages.

http://www.intra-vasc.nl/.

* cited by examiner

DEVICES AND METHODS FOR BLOOD FLOW ASSISTANCE

BACKGROUND OF THE INVENTION

1. Field of the Invention

The present invention relates generally to blood flow assistance. More specifically, the present invention relates to devices and methods for extra-vascular blood flow assistance.

2. Background of the Invention

Maintaining proper blood flow is one of the basic tenets of promoting good health. The heart, being the primary organ responsible for the driving force of blood flow, has the heavy burden of incessantly pumping small volumes of blood in an endless loop within the circulatory system. Thus, it should be expected that any event that affects the proper functioning of the heart would, in turn, affect proper blood flow through the circulatory system, which, in turn, will affect body health. Such events that affect proper heart pumping function include, for example, congenital heart defects, accidents, and various types of surgery.

For example, in one such event, cardiac surgery, the heart often is at least partially damaged so as to need assistance in being able to increase in strength in order to perform its proper pumping function. For example, low cardiac output syndrome following cardiac surgery is not uncommon, and may be caused by impaired cardiac performance due to left, right or biventricular failure.

Despite conventional pharmacologic treatment, some patients having had such procedures require the use of mechanical cardiac support to treat cardiac failure. For adult patients, conventional choices for mechanical cardiac support include, for example, the intra-aortic balloon pump ("IABP") and the ventricular assist device ("VAD"). For children and infants, options are much more limited.

Application of the IABP for infants has a number of drawbacks, including limited hemodynamic effectiveness, difficulty in application, and limited availability. Utilizing a pediatric VAD or extracorporeal life support ("ECLS") may provide greater hemodynamic benefit than the pediatric IABP, but requires expensive equipment, specially trained personnel to deal with the complicated machinery, and has even more limited availability than the pediatric IABP.

The limited effectiveness, technical difficulty, complexity and expense associated with current technology result in suboptimal clinical success for many patients, particularly in pediatric cases. Thus, there is a need for an easy to use, versatile and inexpensive system that provides blood flow assistance that is needed without suffering from the drawbacks of conventional blood flow systems.

SUMMARY OF THE INVENTION

The present invention provides low-profile, implantable blood flow assistance devices or methods that include simple and versatile components, making it ready to use without significant training or preparation time. As used herein and throughout this disclosure, "low profile" means capable of being implanted within areas in the body with minimal interference with surrounding tissue because of the inherent shape of the device, designed to fit within such body areas.

Furthermore, a device or method according to the present invention includes components that readily attach to fluid pumping equipment currently in use in clinics, making it universally acceptable in most clinical environments. Particular exemplary devices include a blood chamber and a fluid chamber that are separated by a flexible membrane that extends into either chamber to affect the volume of blood or fluid. Also, an insertion end is included in particular embodiments that may use a variety of attachment components that simplify, strengthen and anchor the device with respect to body tissue.

In the case of use with pediatric patients, use of a small volume space in conducting extraaortic counterpulsation may be achieved in a manner which addresses the suboptimal effectiveness and technical difficulties associated with the use of conventional technologies. Many other advantages of the present invention are described in more detail below or are apparent to one having ordinary skill in the art upon consideration of the exemplary embodiments presented herein.

In one particular embodiment of the present invention, a device is disclosed for promoting blood flow. The device comprises a blood chamber having a blood chamber port, the blood chamber being in communication with a source of blood; a fluid chamber having a fluid chamber port, the fluid chamber being in communication with a source of fluid pressure; and a flexible membrane separating a portion of the blood chamber from a portion of the fluid chamber. When fluid enters the fluid chamber through the fluid chamber port, the flexible membrane moves further into the blood chamber causing any blood therein to flow out of the blood chamber through the blood chamber port. Alternatively, when fluid exits the fluid chamber through the fluid chamber port, the flexible membrane moves further into the blood chamber causing any blood therein to flow out of the blood chamber through the blood chamber port.

In another embodiment of the present invention, a system is disclosed for promoting blood flow. The device comprises means for storing blood, the means for storing blood being in communication with a source of blood; means for storing fluid, the means for storing fluid being in communication with a source of fluid pressure; and means for controlling blood and fluid storage, the means for controlling blood and fluid storage being in communication with both the means for storing blood and the means for storing fluid. When fluid enters the means for storing fluid, the means for controlling blood and fluid storage causes blood to flow out the means for storing blood. Alternatively, when fluid exits the means for storing fluid, the means for controlling blood and fluid storage causes blood to flow into the means for storing blood.

In yet another embodiment of the present invention, a method is disclosed for promoting blood flow. The method comprises providing a blood chamber having a blood chamber port, the blood chamber being in communication with a source of blood; providing a fluid chamber having a fluid chamber port, the fluid chamber being in communication with a source of fluid pressure; providing a flexible membrane separating a portion of the blood chamber from a portion of the fluid chamber; flowing fluid into the fluid chamber through the fluid chamber port; causing movement of the flexible membrane into the blood chamber; and flowing blood out of the blood chamber through the blood chamber port

DETAILED DESCRIPTION OF THE INVENTION

The present invention includes devices and methods used for blood flow assistance for patients whose cardiac output is too low to maintain a healthy flow of blood through the circulatory system. Using principles of extra-vascular counterpulsation as the primary driving force, various embodiments of the present invention allow for intake of blood from a blood vessel during periods of systole and expel of such intaken blood during periods of diastole. Such intake and expel of blood through a mechanized external device provides a supplemental driving force to enhance the heart's weakened cardiac output. However, exemplary embodiments of the present invention are not limited to counterpulsation pulsation and may also be used in conjunction with the cardiac cycle as is apparent to one having ordinary skill in the art. For example, exemplary devices described herein may be used to assist the right atrium of the heart in generating pulsatile pressure. Other exemplary uses will be described below.

Use of exemplary embodiments of the present invention addresses an important clinical need for simple, effective treatment of postoperative cardiac failure, particularly in pediatric patients. Although such exemplary devices and methods are typically most effective when applied to the aorta, the present invention is not limited to attachment thereto, and may be used in any area of the body that could benefit from assistance in increasing flow of blood. For example, such exemplary devices may be attached to other cardiovascular structures, such as, for example, the pulmonary artery and the heart itself.

Figure 1:
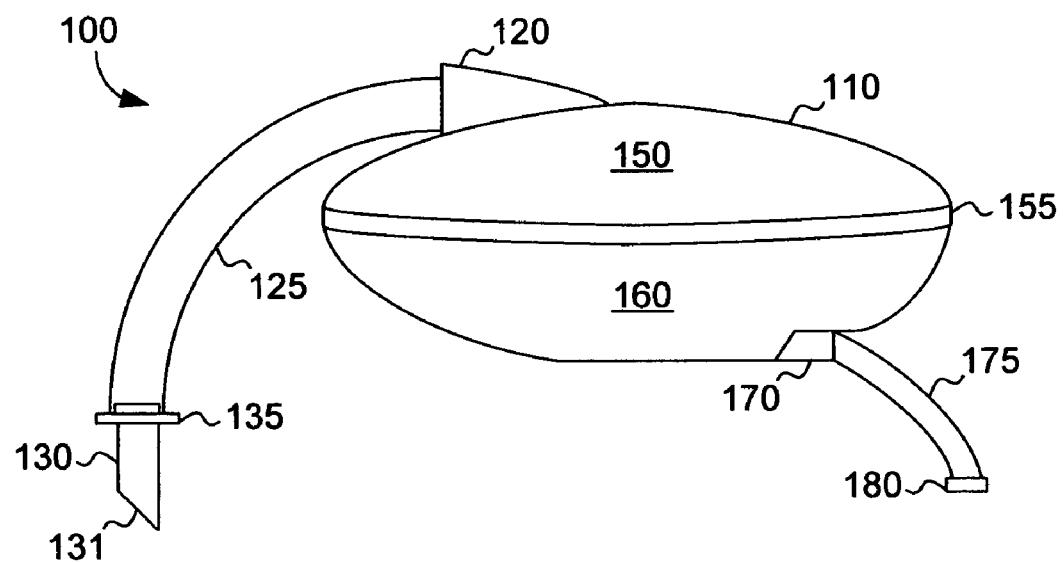
FIG. 1 shows an external perspective view of a blood flow assistance device according to an exemplary embodiment of the present invention.

An exemplary embodiment of the present invention is presented as flow device 100, as shown in FIG. 1, used for promoting flow (and associated pressure) in a circulatory system. Such flow may be either counterpulsation or pulsatile, as deemed by a health care worker for a particular patient. Although device 100 may be used for an adult or child, animal or human, depending on the volume and shape of the device, examples presented herein will be made with particular emphasis to pediatric patients because of the unique and difficult challenges presented in such patients. However, the present invention and its teachings and suggestions are not limited to pediatric patients, or only to humans, but to adults as well as animals.

Device 100 includes an external housing unit 110, which houses one or more chambers. In the example shown in FIG. 1, housing 110 includes a blood chamber 150 and a fluid chamber 160. Blood chamber 150 is shown in this particular embodiment as a spheroid valveless single-port pumping chamber. However, other types of chambers are also possible as long as they are also low profile and biocompatible. Device 100 has a low profile design that allows it to be implantable into a body. For example, device 100 may be implanted in the anterior mediastinal space.

Blood chamber 150 is in communication with a blood chamber port 120 that enables passage of blood into and out of blood chamber 150. Blood chamber port 120 is coupled with a flexible conduit 125, which ends in a rigid tip 130. Although rigid tip 130 is shown having a specific shape in FIG. 1, flow device 100 is not limited to only such an exemplary embodiment and many other types of rigid tips 130 may be also used. Rigid tip 130 has a tip end 131 which may be slanted, as shown in FIG. 1, to allow for easier insertion into body tissue. Such slanted shape is also beneficial in directing flow in a particular direction, such as downstream in a blood vessel. An adaptor end 135 of rigid tip 130 allows coupling of rigid tip 130 to conduit 125.

Rigid tip 130 has the ability to be attached to a blood vessel using conventional suturing techniques (e.g., purse string suturing). Rigid tip 130 design may vary as well as the type of material used. For example, rigid tip 130 may be rigid or flexible, but not so flexible that it provides difficulty in inserting into a blood vessel. Any type of rigid tip 130 may be used according to embodiments of the present invention as long there is an adaptor end 135 that can mate with blood conduit 125. For example, a small caliber tip, which may be in a cannula connector size, may be used to allow quick insertion into body tissue.

The various embodiments of rigid tip 130 design minimize the space required to attach flow device 100 to body tissue, as compared to conventional techniques which require direct sewing of the conduit 125 to the vessel. Some of the embodiments of rigid tip 130 may include, but are not limited to, an anchoring mechanism created or deployed by shape memory materials (e.g., nitinol), expandable wire structures, inverted contact lens shapes or the like. Such varying designs allow for end to side connection of rigid tip 130 to a side of a blood vessel or branch connection of rigid tip 130 directly to a blood vessel branch. A primary advantage of such a type of rigid tip 130 is the ease of insertion into body tissue as compared to partial clamp and sewing to such tissue, which are typically necessary procedures of conventional techniques. Exemplary embodiments of rigid tips and means of anchoring to a blood vessel are presented in FIG. 5 and will be discussed in further detail below.

In certain exemplary embodiments, a flexible membrane 155 separates blood chamber 150 and fluid chamber 160. Such a membrane may be relatively thin or thicker, as long as there is no leakage, and acts as a moving diaphragm to control the sizes of both blood and fluid chambers 150 and 160, respectively. Movement of flexible membrane 155 promotes motion of blood into and out of blood chamber 150 and fluid into and out of fluid chamber 160.

A fluid chamber port 170 allows fluid to enter and exit fluid chamber 160. A flexible fluid conduit 175 is coupled with fluid chamber port 170 and allows for communication between fluid chamber 160 and an outside source of fluid (not shown). A fluid source adaptor 180 connects with an outside source of fluid to create a closed fluid space to allow fluid to be driven into and out of fluid chamber 160. Such outside sources of fluid may include, but are not limited to, rhythmic pumps, IAB pumps, manual pumps, or the like. Such outside fluid may be, for example, air or other inert gas or liquid.

The volume of blood chamber 150 may typically be up to 60 mL for use in pediatric and adult patients. More preferably, a volume size of up to 35 mL will be used to account for most patients. In one particular exemplary embodiment particularly most suitable for pediatric patients, flow device 100 is an air driven bladder-type pump with a flexible membrane 155 separating blood chamber 150 and fluid chamber 160. Its small physical size and small pumping volume (e.g., 10 mL maximum) of flow device 100 could be used more specifically for neonates and infants.

In a particular exemplary embodiment, flow device 100 has a low profile design with a single eccentrically located blood port 120 attached to an 8 mm woven vascular graft 125. Vascular graft 125 may be connected to an ascending aorta or pulmonary artery via rigid tip 130. The material used for vascular graft 125 may be synthetic or natural (e.g., xenografts, cryopreserved or cadaveric fixed conduits). Such materials are not specific to the embodiments of the present invention and may be obtained from appropriate vendors.

Slanted end 131 of rigid tip 130 makes implantation as easy as inserting an arterial cannula into a blood vessel. Alternatively, such a slanted end 131 may be cut off if a sutured anastomosis is desired. The particular location of insertion of rigid tip 130 into a blood vessel should be determined for the most ideal treatment procedure for a particular patient. For example, blood flow device 100 may be attached to the aorta to assist the left ventricle, the pulmonary artery to assist the right ventricle or multiple devices attached to both the aorta and the pulmonary artery for biventricular assistance. Device 100 may also be positioned to assist the right atrium in pulsatile pressure generation. The flexibility of application of devices according to the present invention allows for positioning of such devices anywhere where such assistance is sought.

Flow device 100 is designed to be operated by standard pumping devices, such as a standard IAB pumping console fitted with an adaptor 180 for pediatric IAB. Two devices (for biventricular assistance) may be driven simultaneously from the same IAB console. There is no need for a specialized fluid pump to drive the motion of flow device 100, thereby making such device universally applicable and adaptable to existing hospital and clinic equipment.

As shown in the examples herein, components that are in contact with blood or other body fluid should be biocompatible so as to present no toxic or other ill effects for the patient. Components that are in contact with fluid flow should be airtight to enable proper fluid flow or fluid storage through or within such components, respectively. For example, most or all of flow device 100 may be fabricated from blood-compatible polyurethane using thermoforming (vacuum forming) techniques or injection molding. Materials other than polyurethane may also be used as long as they have properties that are suitable to the function of the current invention. For example, silicone, or other biocompatible plastics or polymers or mixtures thereof may also be used as long as the properties of the material are compatible with the function of device 100.

Device 100 may be constructed as a single unitary piece using, for example, thermoform or RF welding. Alternatively, each of the components in device 100 may be separable, such that particular pieces may be replaced or exchanged. This latter alternative is particularly useful to decrease cost of using an entirely new device 100 for each patient rather than just replacing blood chamber 150 and associated conduit 125 and rigid tip 130 with each new patient. Such modularity of particular components of device 100 also allows for differing shaped and sized components to be used together for a particular patient. Such components may be attached together using standard attaching means, such as, for example, snaps, locks, pins or the like.

In use, flow device 100 shown in FIG. 1 provides improved flow of blood into and out of blood chamber 150 in conjunction with reverse flow of fluid into and out of fluid chamber 160. As shown in a cross section schematic in FIG. 2, housing 210 includes a flexible membrane 255 separating blood chamber 250 from fluid chamber 260. Blood chamber 250 includes a blood chamber port 220 to enable blood to enter and exit chamber 250. Likewise, fluid chamber 260 includes a fluid chamber port 270 to enable fluid to enter and exit chamber 260.

Figure 2A:
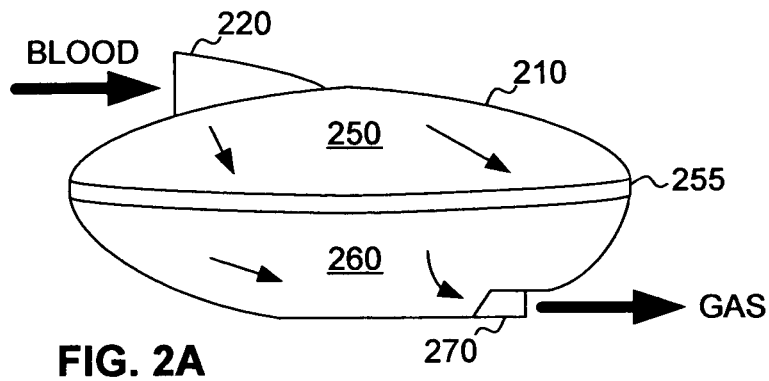
FIG. 2 shows a perspective view of the device shown in FIG. 1, having conduits removed for sake of simplicity, showing various blood and fluid flow movements into and out of chambers within the device.
Figure 2B:
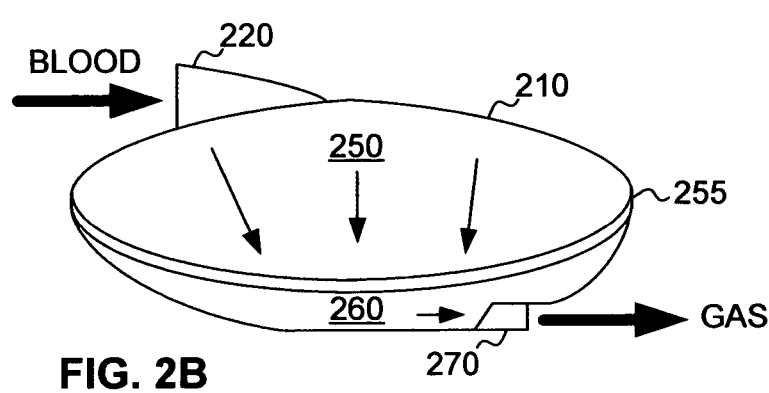

As shown in FIG. 2A, blood enters blood chamber 250 at the beginning of the heart pumping cycle through blood chamber port 220. For example, such blood may be freshly pumped blood flowing out of the left ventricle into the aorta and further into an opening in a rigid tip (not shown) that leads to blood chamber port 220. As blood flows into blood chamber 250, flexible membrane 255 moves downward into fluid chamber 260, which in turn causes any fluid inside fluid chamber 260 to exit through fluid chamber port 270.

A driving force, which may be used to remove fluid from fluid chamber 270, may be, for example, a positive/negative pressure source (not shown) that is attached to a distal end of fluid chamber port 270. As a negative pressure source (e.g., vacuum source) creates the necessary negative pressure necessary to exhaust fluid out of fluid chamber 260, flexible membrane 255 is caused to move further into fluid chamber 260, thereby increasing the volume of blood chamber 250. A sudden increase in volume of blood chamber 250 causes a relative drop in pressure therein, thereby promoting an inflow of blood into blood chamber 250 from a blood flow source, such as the aorta.

As blood enters into blood chamber 250 and fluid exits from fluid chamber 260, flexible membrane 255 extends further into fluid chamber 260. This downward movement shown in FIG. 2B enables a larger volume of blood to enter blood chamber 250. However, after blood chamber 250 is filled, the active exhaust of fluid from fluid chamber 260 is ceased and a reversal of flow motion is initiated. Alternatively, the positive/negative pressure source may be programmed for a particular stroke volume or for a particular stroke rate, upon reaching such volume or maintaining such rate, reversing pressure to reverse fluid flow direction, having a direct influence on blood flow direction. For example, a pediatric stroke volume is about 5 cc to about 10 cc. An exemplary stroke rate may be up to about 150 beats per minute ("bpm"), but more likely about 80–150 bpm. Many other alternative volume and stroke rate combinations are possible and are within the scope and extent of the teachings of the present invention.

Figure 2C:
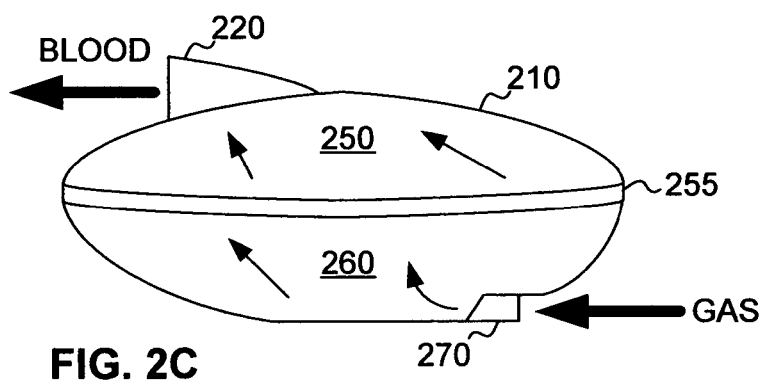

In reverse flow, fluid is pumped into fluid chamber 270 as a direct result of positive pressure in a pressure source (not shown), as shown in FIG. 2C. In such flow, flexible membrane 255 is forced somewhat into blood chamber 250, displacing blood that is in blood chamber 250 and causing it to flow out through blood chamber port 220, and into the original blood source, such as the aorta. Such a reversal of motion may be driven by a reversal of vacuum to pressure switch on the positive/negative pressure source (not shown) in communication with fluid chamber 260. A driving force of fluid into fluid chamber 260 creates the opposite motion of blood in FIG. 2C as compared to FIG. 2A.

Figure 2D:
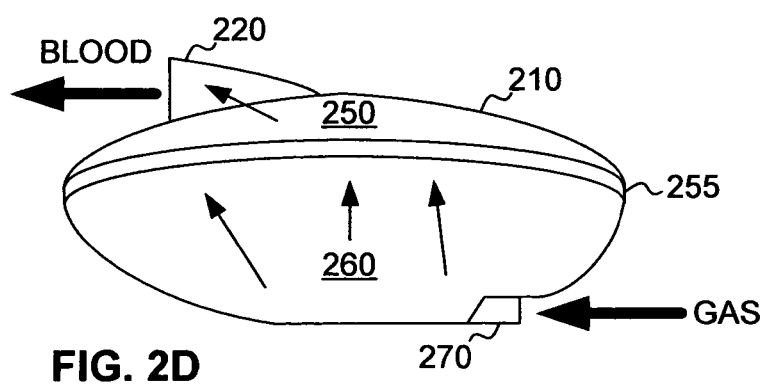

As fluid chamber 260 fills to capacity, as shown in FIG. 2D, the upward movement of flexible membrane 255 reaches a maximum level. In movement toward this position, the rate of displacement from blood chamber 250 slows, and ejection ends. This marks the end of the pumping cycle and the cycle begins with that shown in FIG. 2A. Thus, FIGS. 2A–2D show a typical blood flow pumping cycle used by flow devices according to various embodiments of the present invention.

One of the advantages of the exemplary embodiments of the present invention over that of conventional devices is the low profile shape. The lower profile configuration allows surgeons or other health care workers the option to temporarily place the device within the thorax or to maintain the device outside of the body. Additionally, an externally accessible quick-connect adaptor 180 allows for air inflation/deflation of the chambers of the housing without unneeded access to the working components of the device. In contrast, conventional devices are primarily made for external use only and do not provide the option of placing the flow assistance device within the chest cavity. This additional advantage provides a surgeon with options that would be most beneficial for a particular patient.

There are many advantages to having the ability to implant such a device into the body cavity rather than to maintain it externally. Implantable devices allow for shorter connectors, thereby placing such devices closer to the blood source. As a result, less blood volume is required to fill the conduit, thereby improving the cycling capability or performance of the device. Stated differently, an implantable device according to the present invention allows for improved filling and evacuation of blood chamber 150 as compared to conventional devices because of the reduced residual volume. Decreased travel distances and contact with foreign materials for blood cells cause potentially less blood compatibility or trauma problems.

Another advantage of exemplary embodiments of the present invention over that of conventional devices includes the decreased requirement for space. Less required space for the present invention allows for temporary placement of device into the body. Also, a lower required pumping volume (e.g., priming, stroke volume and tidal volume) decreases the volume of exposed blood volume, which is common for larger devices, which exposed blood volume is larger than the total stroke volume (resulting in blood remaining in graft and chamber at end of pump cycle). Such lower pumping volume is most ideal for pediatric patients.

Another advantage of particular exemplary embodiments of the present invention is in its ellipsoid shape, having a large radius and low profile. Such shape allows for easier insertion into the body without a large requirement of space or the creation of a large bulky area. For example, exemplary embodiments of the present invention may be positioned within the anterior mediastinal space, which small space is suitable only for low-profile shapes. Thus, this ellipsoidal shape is most beneficial in pediatric patients whose bodies do not have enough bulk to house such a device.

Use of a non-rigid polyurethane or any other biocompatible polymer or other synthetic material with a low durometer housing 110 allows the ability to manually de-air the device by pulsing the chamber with fingers. Furthermore, flexibility of housing 110 allows greater opportunity for placement into tight spaces, and allows greater conformance and less compression due to adjacent structures. Such compression may be reduced or eliminated, depending on durometer of material, and is apparent to one having ordinary skill in the art. For example, a durometer range of 20–60 is preferable for materials used in certain exemplary embodiments of the present invention. Finally, the flexibility of positioning flow device 100 allows for greater number of choices for attachment in the body, including, but not limited to, aorta, pulmonary artery or aortic arch vessel, and increased flexibility of choice of placement (e.g., insertion sites).

Although exemplary embodiments shown in FIGS. 1 and 2 have been presented with a particular shape for blood chamber 150, such shape is not a limitation of the present invention. Other shapes may also be used. For example, in some exemplary embodiments of the present invention as shown in FIG. 3, the shape of blood chamber 350 can be invertible. In such embodiments, blood chamber port 320 of blood chamber 350 will be flexible to allow for expansion during the blood ejection period. The shape of chamber 350 and the inversion that occurs during filling and ejection is intended to reduce the local region of stagnation. The blood chamber 350 is intended to remain "seamless" and without areas of significant stagnation of flow during all parts of the filling and ejection periods. Use of a larger exit orifice (e.g., dynamic increase in diameter) results in lower shear stresses and better flow characteristics than a smaller exit orifice.

Figure 3A:
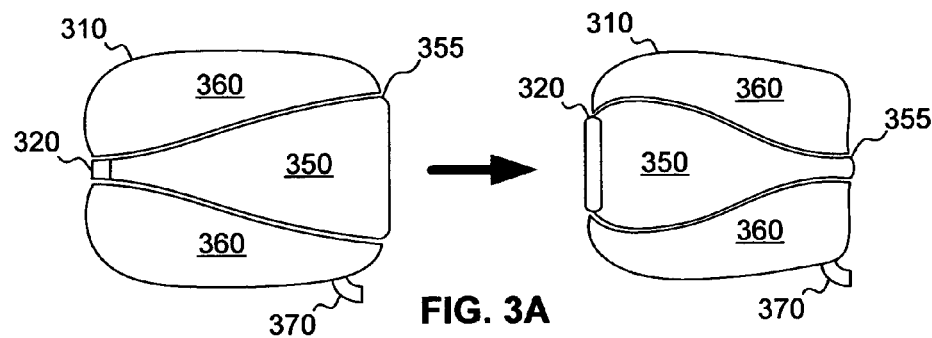
FIG. 3 shows a number of different exemplary embodiments of shapes for a blood chamber with respect to a fluid chamber and changes in such shapes occurring in reaction to blood movement into and out of such a blood chamber.

As shown in FIG. 3A, as blood chamber 350 is being filled with blood, its outer surface 355 which is partially controlled by the shape of fluid chamber 360, which may be controlled by a flexible membrane, is shaped such that blood rapidly flows through blood chamber port 320 and into blood chamber 350. At the end of the filling cycle, the chamber 350 changes in shape, partly through influence of flexible membrane 355, such that blood exits blood chamber 350 through a larger blood chamber port 320. Such inversion allows for better flow characteristics, lower shear stresses (resulting in less potential harm to blood components), and reduced areas of blood stagnation within blood chamber 350.

Figure 3B:
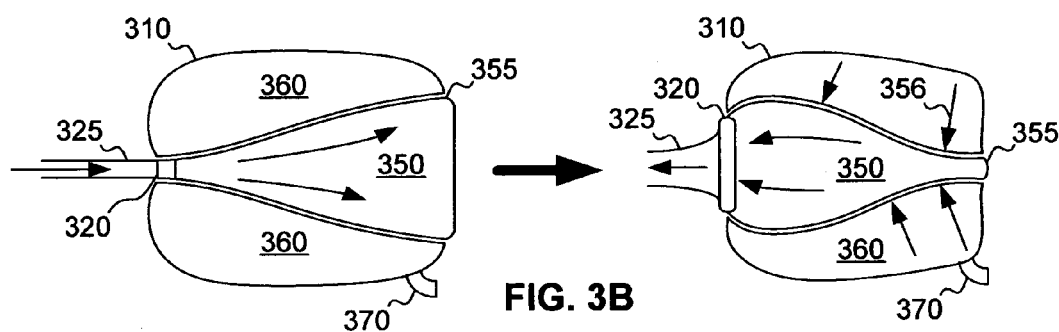

FIG. 3B shows the dynamics of blood flow into and out of blood chamber 350 with more detail. Blood enters through flexible conduit 325 and into blood chamber 350 through blood chamber port 320. At the end of the blood pumping cycle, blood is caused to exit blood chamber 350 by enforcement of forces 356 generated within fluid chamber 360 on flexible membrane 355, causing an enlarged opening in blood chamber port 320 and release of blood back through flexible conduit 325. Such flexible conduit 325 may also enlarge during the blood exit stage, thereby further resulting in decreased imposed shear stresses on the exiting blood.

Such inflow and outflow of blood with respect to blood chamber 350 may be directed by inflow and outflow of fluid with respect to fluid chamber 360 through fluid chamber port 370. As shown in both FIGS. 3A and 3B, blood chamber 350 is at least partially surrounded by fluid chamber 360 which serves to squeeze blood chamber 350 in a rhythmic fashion. These figures are shown through a mid-device plane to show the details of the internal blood and fluid flow.

Figure 3C:
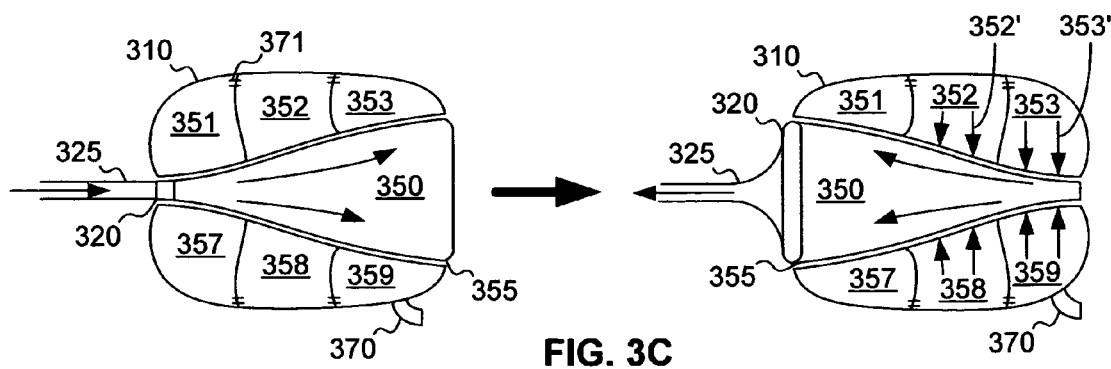

In an exemplary embodiment of the present invention as shown in FIG. 3C, a multi-component element may be used to create staged inflation and deflation patterns. This can be used as a drive mechanism to expel blood in a manner that reduces the potential for stagnation regions within blood chamber 350. In the example shown, housing 310 contains segmented fluid chamber regions 351, 352, 353, 357, 358, and 359, each sharing its some surface area with blood chamber 350.

Such a multiple fluid-chambered mechanism may have sequential inflation/deflation characteristics to prevent areas of stagnation within blood chamber 350. Each has chamber 351, 352, 353, 357, 358 and 359 may be connected to its adjacent chamber through a mutual port 371, thereby allowing uniformity of vacuum and pressure among all chambers as determined by fluid chamber port 370. Alternatively, each chamber 351, 352, 353, 357, 358 and 359 may have its own independent source of positive/negative pressure through an independent port (not shown) which will allow each chamber to expand and contract in a staggered flow pattern.

Alternatively, each fluid chamber may be donut-shaped and positioned about blood chamber 350 in a concentric manner such that fluid chamber 351 is the same as fluid chamber 357, fluid chamber 352 is the same as fluid chamber 358, and fluid chamber 353 is the same as fluid chamber 359. In such a manner, each donut-shaped fluid chamber 351/357, 352/358, and 353/359 is exposed to a source of vacuum or pressure in a sequential manner.

In the example shown in FIG. 3C, pressure force 353' created within concentric fluid chamber 353/359 will serve to push on flexible membrane 355 of blood chamber 350 to promote the exit of blood out through blood chamber port 320. As force 353' increases to promote flow of blood out of the far end of blood chamber 350, force 352' is formed within fluid chamber 352/358 and is imposed on flexible membrane 355 to further promote exit of blood out of blood chamber 350. In such a sequential manner, forces are formed in concentric fluid chambers positioned about blood chamber 350 to systematically and sequentially force blood of chamber 350 in a unidirectional manner.

Although such an example is shown in FIG. 3C with blood chamber 350 having a single blood chamber port 320, the same mechanism may be used for a blood chamber with multiple blood chamber ports such that blood is directed into the chamber through one port (e.g., port 320) and directed out of the chamber through another port (e.g., positioned in far right side of blood chamber 350). Other optional configurations are also possible and apparent to one having ordinary skill in the art, such as a circular dome with a flower/peddle design that inflates/deflates differently during each cycle, thereby altering the blood flow pattern through housing 310.

Figure 4A:
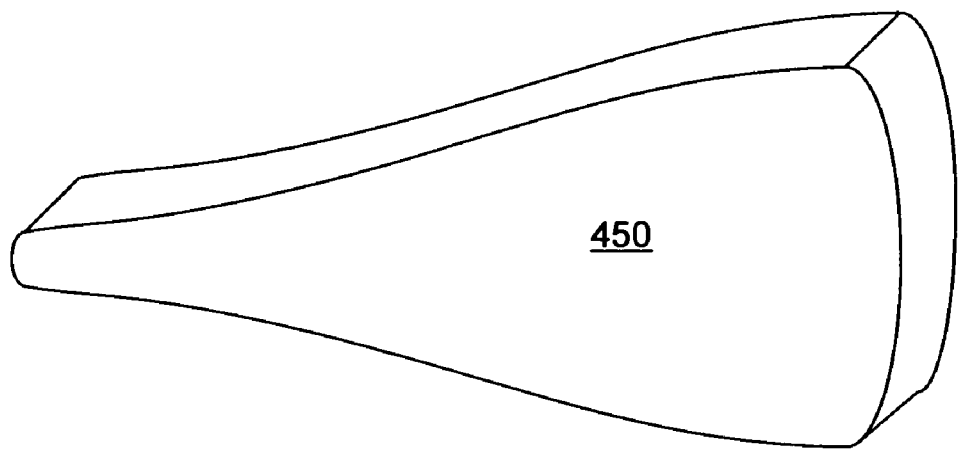
FIG. 4 shows exemplary embodiments of blood chamber shape configurations as used for a blood flow assistance device according to exemplary embodiments of the present invention.
Figure 4B:
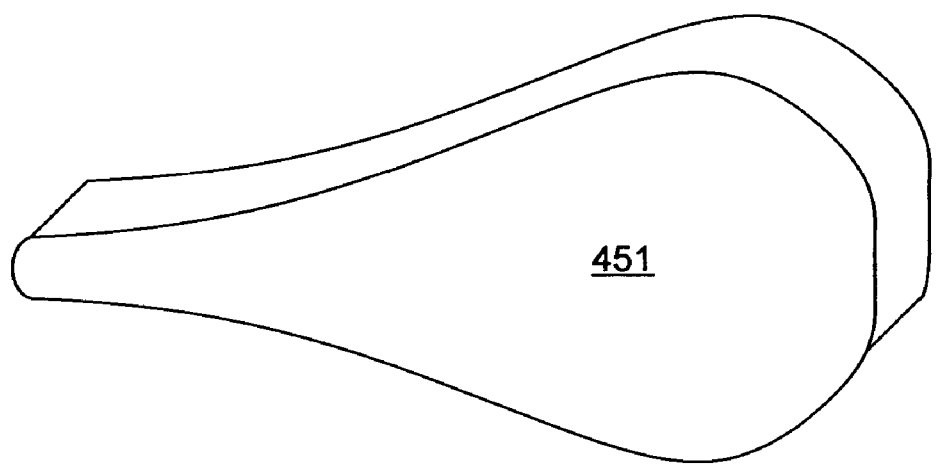

Various exemplary embodiments in the present disclosure have been shown with specific shapes and configurations. However, the present invention is not limited to such exemplary shapes and configurations. For example, blood chamber 350 shown in FIGS. 3A–C has been shown with a distinct shape for exemplary purposes. Many other shapes are also possible for blood chamber 350 and are within the scope of the present invention. As an example, blood chamber 450, shown in FIG. 4A, in the shape of a flask, may also be used. Another non-limiting example is blood chamber 451 shown in FIG. 4B, in the shape of a bulb or teardrop. Other shapes are also possible, apparent to one having ordinary skill in the art, and do not detract from the teachings of this disclosure.

As briefly discussed above, one of the advantages of the exemplary devices and methods according to the present invention is the ease of attachment to a tissue in the body. For example, rigid tip 130 shown in FIG. 1 is designed to be inserted quickly and cleanly into body tissue. In one particular embodiment shown in FIG. 5A, rigid tip 530 is shown in a position such that its rigid tip end 531 is directed through an opening 591 within a blood vessel 590. Such blood vessel may be, for example, an aorta. Rigid tip adaptor 535 secures rigid tip 530 with respect to a conduit (not shown) leading to blood chamber (not shown).

Figure 5A:
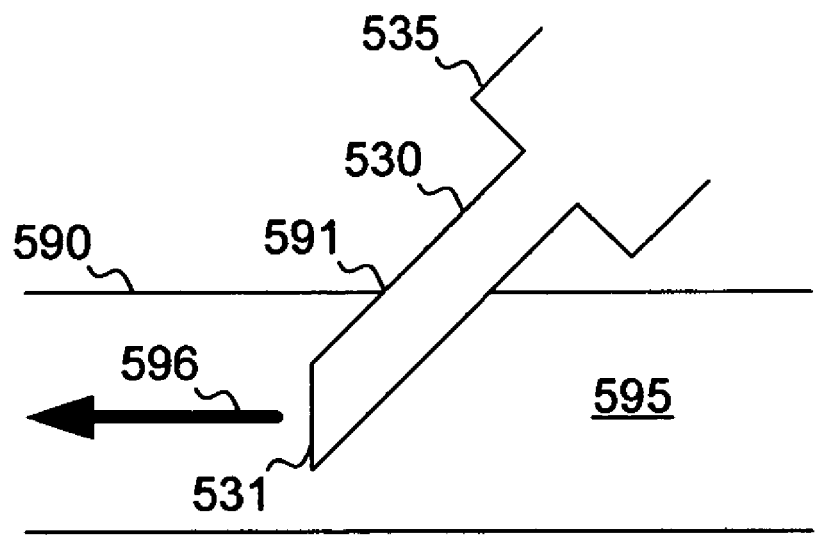
FIG. 5 shows the positioning of a rigid tip of a blood flow assistance device according to exemplary embodiments of the present invention wherein the rigid tip is held in position with respect to a blood vessel through various means, including use of suture and use of an anchoring mechanism.

In the particular example shown in FIG. 5A, blood movement in the direction of arrow 596 flows in the same downstream direction of an open end of rigid tip end 531 to facilitate the flow of blood from a rigid tip 530 down the interior 595 of blood vessel 590. In the particular example shown in FIG. 5A, the rigid tip 530 may be secured in position through various means, including, for example, conventional suturing techniques.

Figure 5B:
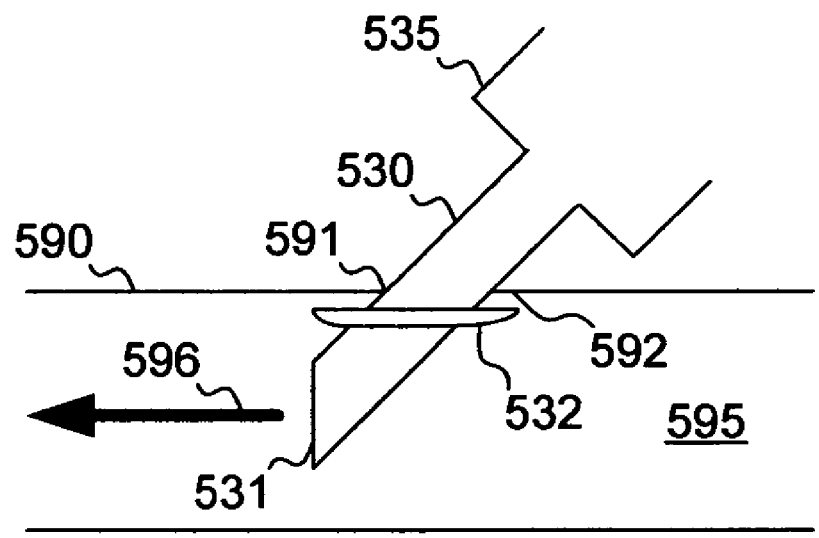

In another exemplary embodiment, as shown in FIG. 5B, rigid tip 530 may be secured in position with respect to a blood vessel 590 such that its rigid tip end 531 is located within the interior 595 of blood vessel 590 without use of sutures. In this exemplary embodiment, rigid tip 530 includes an anchoring mechanism 532 that is convex on its lower surface and flat on its upper surface as shown in FIG. 5B, similar to a contact lens for an eye with an opening in the center. This shape for anchoring mechanisms 532 enables rigid tip 530 to be easily inserted into blood vessel 590 through opening 591 such that the lower convex surface has no edges and slides more easily through opening 591. Anchoring mechanisms 532 may be constructed from a soft, low durometer polymer or material that will minimize tissue trauma as it slides into position through opening 591.

Once anchoring mechanism 532 is positioned within the interior 595 of blood vessel 590, rigid tip 530 may be pulled in an upward position relative to FIG. 5B such that its upper flat surface becomes flush with an interior surface 592 of blood vessel 590. The upper flat surface of anchoring mechanism 532 lays substantially flat against interior surface 592 of blood vessel 590 such that need for a suture anastomosis is reduced or eliminated. Such a rigid tip 530 having anchoring mechanism 532 provides a surgeon or other health care worker with more convenience in quickly inserting and positioning rigid tip 530 in blood vessel 590 of a patient. Such a rigid tip 530 will not easily pop out of blood vessel 590 because anchoring mechanism 532 serves to anchor rigid tip 530 in place, thereby reducing risks of blood loss and injury to a patient if such a device is dislodged during use.

There are many other means of securing rigid tip 530 in position with respect to blood vessel 590 such that rigid tip end 530 is located within the interior 595 of blood vessel 590, other than as shown in FIGS. 5A and 5B. Such other means are within the purview of one having ordinary skill in the art and within the scope of the present invention.

Devices and methods according to the present invention have many advantages over that of related art. Many of such advantages are described above or and inherent or intrinsic to the invention. An advantage of the present invention that distinguish it from conventional devices relates to the flexibility of such devices, in that they may have a variety of different shapes and are not limited to ellipsoidal sacs. Exemplary devices described herein also may have continuous contour shapes (e.g., spheroid, bulb, flask) to aid in improved fluid handling. Such varying shapes and positioning of blood chamber ports reduce trapping of blood with the blood chamber and reduce stagnation regions.

Many uses of devices according to the present invention are possible and within the purview of one having ordinary skill in the art. One particular example is presented here. Cardiopulmonary bypass used in conventional coronary artery bypass surgery introduces risk of complications. In order to reduce risk, the trend is moving towards off-pump coronary artery bypass ("OPCAB"). However, manipulation and rotation of the beating heart to gain access to the epicardial vessels may lead to blood pressure and perfusion instability. This may be due to kinking of the right ventricle when the posterior aspect of the heart is exposed, or left ventricular dysfunction when the heart is elevated or displaced to the right to expose the left lateral aspect of the heart.

An exemplary device according to the present invention may be used in the above example as a procedure-enabling counterpulsation assist device to provide blood pressure and flow support for OPCAB procedures, permitting the operation to be completed without cardiopulmonary bypass. An exemplary device may be placed on the pulmonary artery for right ventricular assistance, on the aorta for left ventricular assistance, or on both simultaneously for biventricular assistance. The devices may be used to temporarily support blood pressure and flow during the procedure, and removed at completion of the procedure.

Yet another exemplary use of device may be to provide temporary pulsatile cardiac support during and operations for repair of congenital cardiac disease. For example, the device may be attached to the right atrium to generate pulsatile pressure for assisting pulmonary blood flow after construction of a shunt from right atrium to pulmonary artery in patients with tricuspid atresia or right heart hypoplasia. In this application, the device may be operated with or without synchronization to the cardiac cycle.

The foregoing disclosure of the preferred embodiments of the present invention has been presented for purposes of illustration and description. It is not intended to be exhaustive or to limit the invention to the precise forms disclosed. Many variations and modifications of the embodiments described herein will be apparent to one of ordinary skill in the art in light of the above disclosure. The scope of the invention is to be defined only by the claims appended hereto, and by their equivalents.

Further, in describing representative embodiments of the present invention, the specification may have presented the method and/or process of the present invention as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process of the present invention should not be limited to the performance of their steps in the order written, and one skilled in the art can readily appreciate that the sequences may be varied and still remain within the spirit and scope of the present invention.

We claim:

1. A low-profile implantable device for promoting blood flow, the device comprising:
   a low-profile, non-rigid housing;
   a blood chamber within the housing having a blood chamber port, the blood chamber being adapted to communicate with a source of blood;
   a fluid chamber within the housing having a fluid chamber port, the fluid chamber being in communication with a source of fluid pressure; and
   a flexible membrane separating a portion of the blood chamber from a portion of the fluid chamber;
   wherein when fluid enters the fluid chamber through the fluid chamber port, the flexible membrane moves further into the blood chamber causing any blood therein to flow out of the blood chamber through the blood chamber port; and
   wherein when fluid exits the fluid chamber through the fluid chamber port, the flexible membrane moves further into the fluid chamber causing blood to flow into the blood chamber through the blood chamber port.

2. The device of claim 1, further comprising:
   a blood conduit in communication with the blood chamber port at one end.

3. The device of claim 2, further comprising:
   a tip attached to the blood conduit at an end opposite to the end where the blood chamber port is attached.

4. The device of claim 3, wherein the tip is attachable to body tissue without need for a suture anastomosis.

5. The device of claim 3, wherein the tip has an anchoring mechanism adapted to attach the tip to body tissue.

6. The device of claim 1, wherein the blood chamber has a maximum volume capacity of 60 mL.

7. The device of claim 1, wherein the blood chamber has a maximum volume capacity of 35 mL.

8. The device of claim 1, wherein the blood chamber has a maximum volume capacity of 10 mL.

9. The device of claim 1, further comprising:
   a fluid conduit in communication with the fluid chamber port at one end and the source of fluid pressure at another end.

10. The device of claim 1, wherein such device is implantable within the anterior mediastinal space.

11. The device of claim 1, wherein the source of blood is selected from a group consisting of aorta, pulmonary artery and heart.

12. The device of claim 1, wherein the housing is ellipsoid.

13. The device of claim 1, wherein the blood chamber is spherical.

14. The device of claim 1, wherein the blood chamber is valve-less.

15. The device of claim 1, wherein the blood chamber port is eccentrically located in the blood chamber.

16. The device of claim 1, wherein the fluid chamber comprises a plurality of fluid chambers connected in series.

17. A low-profile implantable device for promoting blood flow, the device comprising:
   means for housing, wherein the means for housing is non-rigid;
   means for storing blood within the means for housing, the means for storing blood being adapted to communicate with a source of blood;
   means for storing fluid within the means for housing, the means for storing fluid being in communication with a source of fluid pressure; and
   means for controlling blood and fluid storage, the means for controlling blood and fluid storage being in communication with both the means for storing blood and the means for storing fluid;
   wherein when fluid enters the means for storing fluid, the means for controlling blood and fluid storage causes blood to flow out the means for storing blood; and
   wherein when fluid exits the means for storing fluid, the means for controlling blood and fluid storage causes blood to flow into the means for storing blood.

18. The device of claim 17, further comprising:
   means for transporting blood in communication with the means for storing blood.

19. The device of claim 18, further comprising:
   means for collecting blood in communication with the means for transporting blood.

20. The device of claim 19, wherein the means for collecting blood is attachable to body tissue without need for a suture anastomosis.

21. The device of claim 19, wherein the means for collecting blood includes a means for locking that is adapted to lock the means for collecting blood onto body tissue.

22. The device of claim 17, wherein the means for storing blood has a maximum volume capacity of 60 mL.

23. The device of claim 17, wherein the means for storing blood has a maximum volume capacity of 35 mL.

24. The device of claim 17, wherein the means for storing blood has a maximum volume capacity of 10 mL.

25. The device of claim 17, further comprising:
means for transporting fluid in communication with the means for storing fluid and the source of fluid pressure.

26. The device of claim 17, wherein such device is implantable within the anterior mediastinal space.

27. The device of claim 17, wherein the source of blood is selected from a group consisting of aorta, pulmonary artery and heart.

28. The device of claim 17, wherein the means for housing is ellipsoid.

29. The device of claim 17, wherein the means for storing blood is spherical.

30. The device of claim 17, wherein the means for storing blood is valve-less.

31. The device of claim 17, wherein the blood chamber port is eccentrically located in the blood chamber.

32. The device of claim 17, wherein the fluid chamber comprises a plurality of fluid chambers connected in series.

33. A method of promoting blood flow, the method comprising:
providing a low-profile, non-rigid housing;
providing a blood chamber within the housing having a blood chamber port, the blood chamber being adapted to communicate with a source of blood;
providing a fluid chamber within the housing having a fluid chamber port, the fluid chamber being in communication with a source of fluid pressure;
providing a flexible membrane separating a portion of the blood chamber from a portion of the fluid chamber;
flowing fluid into the fluid chamber through the fluid chamber port;
causing movement of the flexible membrane into the blood chamber; and
flowing blood out of the blood chamber through the blood chamber port.

34. The method of claim 33, further comprising:
providing a blood conduit in communication with the blood chamber port at one end.

35. The method of claim 34, further comprising:
providing a tip attached to the blood conduit at an end opposite to the end where the blood chamber port is attached.

36. The method of claim 35, further comprising:
attaching the tip to body tissue without use of sutures anastomosis.

37. The method of claim 35, wherein the tip has a locking mechanism that attaches the tip to body tissue.

38. The method of claim 33, wherein the blood chamber has a maximum volume capacity of 60 mL.

39. The method of claim 33, wherein the blood chamber has a maximum volume capacity of 35 mL.

40. The method of claim 33, wherein the blood chamber has a maximum volume capacity of 10 mL.

41. The method of claim 33, wherein the blood chamber and the fluid chamber are implantable within the anterior mediastinal space.

42. The method of claim 33, wherein the blood flow is promoted in the source of blood, which is selected from a group consisting of aorta, pulmonary artery and heart.

43. The method of claim 33, wherein the housing is ellipsoid.

44. The method of claim 33, wherein the blood chamber is spherical.

45. The method of claim 33, wherein the blood chamber is valve-less.

46. The method of claim 33, wherein the blood chamber port is eccentrically located in the blood chamber.

47. The method of claim 33, wherein the fluid chamber comprises a plurality of fluid chambers connected in series.

* * * * *